United States Patent [19]

Jeromin et al.

[11] Patent Number: 4,595,461
[45] Date of Patent: Jun. 17, 1986

[54] PROCESS FOR THE NON-DEGENERATIVE DISTILLATION OF FATTY ACIDS

[75] Inventors: Lutz Jeromin, Hilden; Wilhelm Johannisbauer, Erkrath; Klaus Thorausch, Duesseldorf, all of Fed. Rep. of Germany; Franjo Skrapac, Perth, Australia; Helmüt Hartmann, Langenfeld, Fed. Rep. of Germany; Karl Hentschel, Duesseldorf, Fed. Rep. of Germany; Otto Michel, Langenfeld, Fed. Rep. of Germany

[73] Assignee: Henkel Kommanditgesellschaft auf Aktien, Duesseldorf, Fed. Rep. of Germany

[21] Appl. No.: 599,089

[22] Filed: Apr. 11, 1984

[30] Foreign Application Priority Data

Jun. 23, 1983 [DE] Fed. Rep. of Germany ....... 3322535

[51] Int. Cl.$^4$ .................. B01D 1/22; B01D 3/38; C11C 1/08
[52] U.S. Cl. .................. 203/72; 203/76; 203/77; 203/87; 203/93; 203/DIG. 14; 203/DIG. 19; 203/DIG. 25; 202/155; 202/186; 202/158; 260/419
[58] Field of Search .................. 203/91, 87, 72, 76, 203/77, 89, 92, 93, 96, 95, 97, 98, 94, DIG. 19, DIG. 25, 99, 14, DIG. 14; 260/428, 419; 202/176, 236, 234, 158, 153, 186, 155; 562/606

[56] References Cited

U.S. PATENT DOCUMENTS

| | | | |
|---|---|---|---|
| 2,224,984 | 12/1940 | Potts et al. | 260/419 |
| 2,564,078 | 8/1951 | Pyle | 202/158 |
| 2,804,427 | 8/1957 | Suriano | 260/419 |
| 3,644,179 | 2/1972 | Knoer et al. | 203/72 |
| 3,697,387 | 10/1972 | Munch | 203/72 |
| 4,076,700 | 2/1978 | Harada et al. | 203/72 |
| 4,089,880 | 5/1978 | Sullivan | 260/419 |
| 4,141,799 | 2/1979 | Thelen | 203/72 |
| 4,166,773 | 9/1979 | Higley et al. | 203/72 |

Primary Examiner—Wilbur Bascomb
Attorney, Agent, or Firm—Ernest G. Szoke; Henry E. Millson, Jr.; Mark A. Greenfield

[57] ABSTRACT

A process for the nondegenerative distillation of $C_6$–$C_{24}$-fatty acids, of the type obtained by splitting natural fats and oils or by synthetic processes, such as for example the oxidation of paraffins, the crude product is thermally dried under reduced pressure, the dried and heated crude product is subjected to fractional evaporation in falling-film evaporators, optionally in the presence of superheated steam, and the various vapor fractions are deposited in condensers. The thermal drying process is conducted at a temperature of 60°–80° C. and a pressure of 90–100 mbars. The dewatered crude product is fractionated in a film-forming evaporator and, after distillation, passes to a rectification column which condenses the low boiling constituents as the main runnings.

8 Claims, 1 Drawing Figure

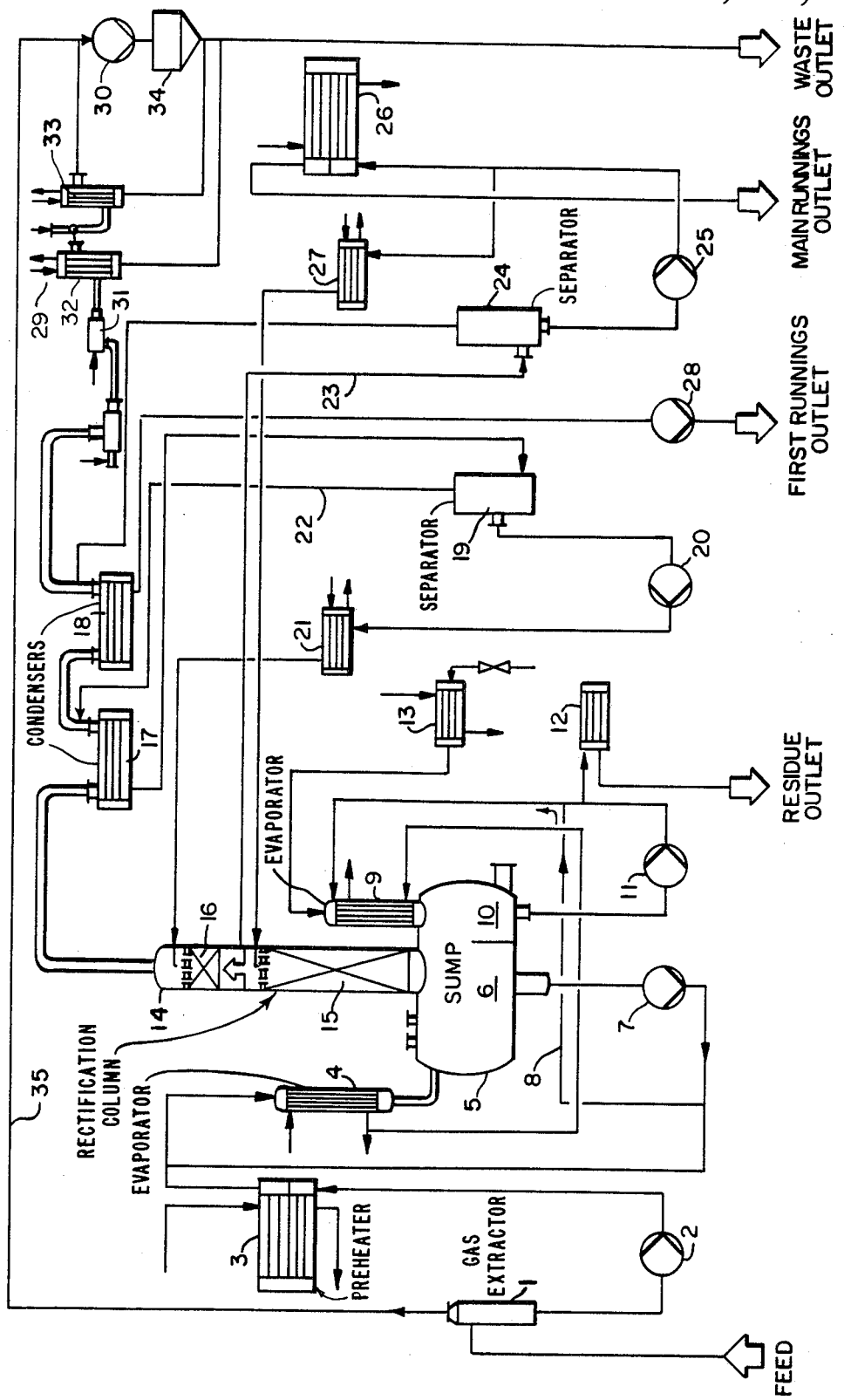

PROCESS FOR THE NON-DEGENERATIVE DISTILLATION OF FATTY ACIDS

BACKGROUND OF THE INVENTION

1. Field of the Invention

This invention relates to an improved process for the non-degenerative distillation of $C_6$–$C_{24}$-fatty acids, of the type obtained by splitting natural fats and oils or by synthetic processes, such as for example the oxidation of paraffins, by thermally drying the crude product under reduced pressure, subjecting the dried and heated crude product to fractional evaporation in falling-film evaporators, optionally in the presence of superheated steam, and depositing the various vapor fractions in condensers.

2. Statement of the Related Art

In addition to a mixture of free fatty acids, fatty acids derived from the hydrolytic splitting of natural fats or of oils on an industrial scale still contain unsplit fatty acid glycerides and substances of the type which accompany fats, such as sterols, phosphatides, polymerized fatty acids and other decomposition products, and also further impurities. In order to remove the undesirable impurities, which are partly responsible for undesirable discoloration, poor color stability and an unpleasant odor of the products, split fatty acids are subjected to distillation.

The distillation of fatty acids has long been carried out on an industrial scale. The first fatty acid distillation units consisted of retorts directly heated by smoke gases and operated under normal pressure. Since the crude fatty acids to be distilled were exposed to very high temperatures, resulting in partial decomposition or polymerization, the distillates obtained were more or less heavily discolored and, in addition, had an unpleasant odor. The quality of the distillates thus produced no longer satisfies current requirements.

In order to obtain distillates of high quality from crude split fatty acids, the distillation process has to be carried out at low distillation temperatures and, hence, under high vacuum with as short a residence time of the crude product to distillation as possible. On an industrial scale, distillation is generally carried out at 2 to 10 mbars and at temperatures of up to about 260° C. (Ullmanns Enzyklopadie der technischen Chemie, Vol 11, pages 533 et seq, Verlag Chemie Weinheim, 1976).

Oils and fatty acids can be purified and decolored by adsorption processes. The most widely used adsorbents are natural and/or activated Fuller's earths. Active carbon is also used in some cases. The disadvantage of these adsorption techniques is that the bleaching materials used are relatively expensive and absorb a certain quantity of the product fatty acids which, in some cases, drastically reduces the yields.

Among the distillation-based purification processes, in almost all of which steam is now added to a greater or lesser extent to reduce the partial pressure and, hence, the boiling point of the fatty acids, there are a number of processes which use further additives during distillation. U.S. Pat. No. 2,583,028 describes the use of boron trifluoride, U.S. Pat. No. 3,833,629 describes the use of aromatic carboxylic acids, Japanese published Patent Application No. 7408-78 and U.S. Pat. No. 3,471,536 describe the use of aromatic or aliphatic amino compounds and British Patent No. 2,032,918 describes the use of reducing metals and hydroxides thereof. All these processes, which are based on separation of fatty acids by distillation in the presence of the above-mentioned additives, are attended by the disadvantage of more or less heavy product losses. In addition, corrosion problems occasionally affect those parts of the apparatus which come into contact with the crude mixtures at elevated temprature.

SUMMARY OF THE INVENTION

The present invention provides a process in which fatty acids of natural origin can be freed from undesirable impurities and separated from one another by distillation in high yields in a single stage carried out at low temperatures and with short residence times, the products obtained being characterized by reproducible color quality, high color stability and by a better odor than the fatty acid fractions obtained by known processes.

Another provision of the present invention is the development of an improvement in the process for the non-degenerative distillation of $C_6$–$C_{24}$-fatty acids selected from the group consisting of the type obtained by hydrolytically splitting natural fats and oils and the type obtained by synthetic processes, by thermally drying the crude product under reduced pressure, subjecting the dried and heated crude product to fractional evaporation in falling-film evaporators, optionally in the presence of superheated steam, and depositing the various vapor fractions in condensers. The improvement comprises essentially of (a) conducting the drying process by heating to a temperature of 60° to 80° C. under a pressure of from 90 to 100 mbars, (b) heating the dried crude product to a temperature of 212° to 224° C. under a pressure of from 5 to 20 mbars to evaporate the low-boiling fraction in a first falling-film evaporator, (c) distilling the liquid residue with recirculation distillation to completion, (d) passing the vapors through a rectification column, whose baffles show a pressure loss of at most 1 mbar/m of packing height at a comparable air flow velocity of at least 2 m/s, the column comprising at least 2 separation stages, the second stage having at least three sub-stages, (e) condensing the vapors in two sequential condensers, (f) returning the condensate from the first condenser to the head of the rectification column, (g) drawing off the main runnings as a sidestream from the rectification column, (h) returning a partial return flow from the sidestream beneath the outlet for the main runnings, and (i) continuously removing a small quantity of residue from the second, circulation-type faling-film evaporator.

BRIEF DESCRIPTION OF THE DRAWING

The FIGURE is a flow diagram of the process of the invention.

DETAILED DESCRIPTION OF THE INVENTION

The present invention relates to an improved process for the non-degenerative distillation of $C_6$–$C_{24}$-fatty acids, of the type obtained by hydrolytically splitting natural fats and oils or by synthetic processes, such as the oxidation of paraffins, by thermally drying the crude product under reduced pressure, subjecting the dried and heated crude product to fractional evaporation in falling-film evaporators, optionally in the presence of superheated steam, and depositing the various vapor fractions in condensers, characterized in that (a) the thermal is carried out at 60° to 80° C. under a pressure of from 90 to 100 mbars, (b) for evaporation, the low-boiling fraction of the dried crude product is heated to 212° to 224° C. under a pressure of from 5 to 20 mbars, (c) the liquid residue is with recirculation distilling to completion, (d) the vapors flow through a rectification column, whose baffles show a pressure loss of at most 1 mbar/m of packing height at a comparable air flow velocity of at least 2 m/s, the column comprising at least 4 separation substages, one in an upper stage and three in a lower stage, (e) the vapors are deposited in two sequential condensers, (f) the condensate from the first condenser is returned to the head of the rectification column, (g) a small quantity of first runnings is drawn off from the second condenser, (h) a return flow from the sidestream is reintroduced beneath the outlet for the main runnings and (i) a small quantity of residue is continuously removed from the second, circulation-type falling-film evaporator.

More particularly the present invention relates to an improvement in the process for the non-degenerative distillation of $C_6$-$C_{24}$-fatty acids selected from the group consisting of the type obtained by hydrolytically splitting natural fats and oils and the type obtained by synthetic processes, by thermally drying the crude product under reduced pressure, subjecting the dried and heated crude product to fractional evaporation in falling film evaporators, optionally in the presence of superheated steam, and depositing the various vapor fractions in condensers, the improvement consisting essentially of (a) conducting the drying process at a temperature of 60° to 80° C. under a pressure of from 90 to 100 mbars, (b) heating the dried crude product to a temperature of 212° to 224° C. under a pressure of from 5 to 20 mbars to evaporate the low-boiling fraction in a first falling-film evaporator, (c) distilling the liquid residue to completion, (d) passing the vapors through a rectification column, whose the baffles show a pressure loss of at most 1 mbar/m of packing height at a comparable air flow velocity of at least 2 m/s, the colmun comprising at least 4 separation sub-stages, (e) condensing the vapors in two sequential condensers, (f) returning the condensate from the first condenser to the head of the rectification column, (g) drawing off the main runnings as a sidestream from the rectification column, (h) returning a partial return flow from the sidestream beneath the outlet for the main runnings, and (i) continuously removing a small quantity of residue from the second, circulation-type falling-film evaporator.

The rectification and purification of the fatty acids feed takes place in a single rectification column after drying and preheating. The sump product is distilled to completion in a falling-film evaporator connected to the column. A dark red, unpleasant-smelling low-boiling fraction separated off by partial condensation is removed overhead. This fraction consists inter alia of low molecular weight hydrocarbons, methyl ketones and aldehydes. The separation of the crude fatty acid from the dirt-containing, unpleasant-smelling fraction takes place in a single passage.

The process according to the present invention provides fatty acids or high color quality and stability. Compared with the known processes, however, products distinguished by a faint, but pleasant odor are obtained in a higher yield.

The rectification column used in the process according to the invention is divided into two, functionally different stages. The upper stage of at least one substage between the head and the sidestream outlet is used for concentrating the low-boiling fractions at the head of the column and for condensing the main runnings. The lower stage, preferably having at least three substages, is used for the separation of high-boiling fractions and for removing droplets entrained from the falling-film evaporators.

The concentration of the low-boiling fractions at the head and of the high-boiling fractions in the sump of the column requires a certain number of separation stages. Baffles in the form of plates or column packings are normally used for forming these separation sub-stages. However, baffles such as those normally used cause a loss of pressure in the column which leads to a higher sump pressure and hence to a higher sump temperature with adverse effects on the color, odor and yield of the distilled fatty acid.

The process according to the invention was actually made possible by the development of baffles characterized by a low pressure loss and a good separating effect. In the context of the invention, baffles producing a minimal pressure loss are understood to be baffles which produce a pressure loss of at most 1 mbar/m at a comparable air flow velocity of 2 m/s. Baffles such as these include metal Pall rings, but especially fabric packings or standard plate packings, such as those available commercially in Germany under the trademarks BX-Packung and Mellapak.

In other respects, the structure of the rectification column corresponds to the usual constructions consisting of: supporting grid, packing, cover grid, distribution plate (main runnings-return flow) and collecting plate (main runnings) in the lower section and supporting grid, packing, cover grid, distribution plate (first runnings return flow) in the upper section.

The grids and plates are streamlined with the same object of minimizing the pressure loss.

The product flow of the process according to the invention is shown in detail in the accompanying flowchart. In the flowchart the following are identified:

| Reference No. | Item |
| --- | --- |
| 1. | gas extractor and dryer |
| 2. | feed pump |
| 3. | preheater |
| 4. | first falling-film evaporator |
| 5. | divided liquid collector |
| 6. | sump |
| 7. | sump pump to head of 4 but some or all can be diverted by |
| 8. | bypass line to head of 9 |
| 9. | second circulation falling-film evaporator |
| 10. | residue sump |

| Reference No. | Item |
| --- | --- |
| 11. | residue sump pump |
| 12. | residue condenser |
| 13. | steam heater for injection of steam in the head of 9 |
| 14. | rectification column |
| 15. | second (lower) separation stage |
| 16. | first (upper) separation stage |
| 17. | first outlet condenser |
| 18. | second outlet condenser |
| 19. | first vapor separator and collector |
| 20. | return pump |
| 21. | first heat exchanger |
| 22. | return line |
| 23. | main runnings line |
| 24. | second vapor separator and collector |
| 25. | main runnings pump |
| 26. | main runnings condenser |
| 27. | second heat exchanger |
| 28. | first runnings pump |
| 29. | vacuum pump assembly |
| 30. | water ring pump |
| 31. | steam jet unit |
| 32. | first pump condenser |
| 33. | second pump condenser |
| 34. | waste water collector |
| 35. | vacuum pipe |

The crude fatty acid mixture is transferred from the tanker to the gas extractor and dryer 1. Dissolved gases are removed in vacuo from the fatty acid. At the same time, the water present in the crude mixture is evaporated. The gases and vapors released are removed through a vacuum pipe 35 which leads to the water ring pump 30.

A pressure of 90 to 110 mbar prevails in the gas extractor for a temperature of 60° to 80° C.

The feed pump 2 forces the crude fatty acid through a preheater 3 heated with steam under a pressure of 4 bars. The feed leaves the preheater 3 with a temperature of 140° to 150° C. and, from there, flows into the first falling-film evaporator 4, which is heated by a liquid mixture of biphenyl and diphenyl ether or ditolyl ether isomers used as a heat transfer agent in the range of 200° to 400° C. A high percentage of the fatty acids in the mixture evaporates at a temperature of from 212° to 224° C. under a pressure of from 5 to 20 mbars.

That part of the feed which is not evaporated is collected at the bottom of sump 6 of the divided liquid collector 5 and is pumped by the sump recirculation pump 7 back to the head of the falling-film evaporator 4. Optionally a part or all of the sump liquid can be pumped to a head of the second falling-film evaporator 9 by bypass line 8. The liquid in the residue sump 10 of the divided liquid collector 5 is pumped via a level governor and residue sump pump 11 to the head of the second falling-film evaporator 9. The second falling-film evaporator 9 is also of the recirculation type. A relatively small quantity of residue is continuously removed from this circuit via a level governor and a residue condenser 12. Where the presence of steam is desired it can be inserted into the head of the second falling-film evaporator 9 by means of the steam heater 13. Generally from 0 to 10%, by weight of the total feed, of steam is employed.

Since the rectification column 14 is divided into upper and lower stages 15 and 16, each of which are equipped with baffles producing a minimal pressure loss, the sump pressure is so low that, basically, there is no need for any further reduction in the partial pressure of the fatty acid mixture by steam in order to obtain the desired quality in regard to the color and odor of the products. If a further improvement in product qualiy is required, it may be obtained by adding superheated steam in a quantity of at most 10%. The object of adding superheated steam is, above all, to deodorize the fatty acid should this be necessary.

The first and second falling-film evaporators 4 and 9 are operated at a constant heated liquid feed temperature. The temperatures of the fatty acid on leaving the evaporators are regulated to avoid overheating of the fatty acid.

The vapor produced in the first and second evaporators 4 and 9 flows through the rectification column 14. This column is filled with Pall rings or standard column packings and has at least four separation sub-sections, at least one in the upper stage 16 and at least three sub-sections (not shown) in the lower stage 15. The column 14 is mounted on the divided liquid collector 5 which is divided by a metal plate so that sump 6 and residue sump 10 are not mixed. The vapors accumulating at the head of the column are cooled in first and second outlet condensers 17 and 18 arranged consecutively.

Most of the vapors are condensed first outlet in the condenser 17 and delivered at a certain temperature as first runnings return flow to the head of the rectification column 14 via a first vapor separator and collector 19, a return pump 20 and a first heat exchanger 21. The separated vapor is returned to the line entering the second outlet condenser 18 via line 22.

Beneath the head of the column 14, the low-boiling constituents of the vapors are concentrated and the main runnings condensed in the upper stage 16. These main runnings are removed approximately one separation sub-stage beneath the head of the column and flow via line 23 into a second vapor separator and collector 24, from which the main runnings can be pumped out of the installation by the main runnings pump 25 via a main runnings condenser 26 to the main runnings outlet. A small proportion of these main runnings is delivered as return flow to the column 14 beneath the sidestream outlet in the lower stage 15 via the second heat exchanger 27. In the lower stage 15 of the column 14, entrained droplets of liquid are separated and returned to the sump 6 of the divided liquid collector 5 and high-boiling, colored constituents are separated off by rectification.

In the second outlet condenser 18, the rest of the vapors are condensed and then removed via the first runnings pump 28.

The installation also comprises a three stage assembly vacuum pump 29 consisting of a steam jet unit 31 with first and second pump condensers, 32, 33, respectively a water ring pump 30 and a waste water collector 34, leading to a waste outlet.

The invention is illustrated by the following examples.

The process according to the invention was tested on fatty acid mixtures obtained from the splitting of tallow (Example 1) and also on residual fatty acid from the fat splitting of the first distillation residues (Example 2). Approximately 85% of olein fatty acids of tallow consist of oleic or stearic acid. This is the feed employed in Example 1. Approximately 66% of residual fatty acid consists of oleic or stearic acid, the remainder consisting mainly of palmitic and palmitoleic acid. This is the feed employed in Example 2.

The colors of the fatty acids were measured by the Lovibond method in a 5¼″-cuvette.

Color quality was assessed by means of heating tests. To this end, samples of the products obtained by the process according to the invention were introduced to a level of 5 cm into a 125 ml wide-necked glass beaker and uniformly stored for 72 hours at 60° C. in a heating cabinet. Color was assessed as indicated.

The odor of the samples was qualitatively assessed by comparison with samples from conventional production units.

EXAMPLE 1

| Feed: Tallow fatty acid | | |
|---|---|---|
| Pressure | 3 mbars | column head |
|  | 9 mbars | column sump |
| Temperature | 216° C. | first falling-film evaporator 4 |
|  |  | second falling-film evaporator 9 |
| Steam | 8% | of the feed |
| First runnings removed | 2% | of the feed |
| Main runnings return flow | 20% | of the main runnings |
| Color | 4 yellow 0.6 red | (Lovibond 5¼″) |
| Acid number of the residue | 85 |  |
| Odor, main runnings | faint, pleasant |  |

EXAMPLE 2

| Feed: Residual fatty acid | | |
|---|---|---|
| Conditions same as in Example 1 except for | | |
| Main runnings return flow | 50% | of the main runnings |
| Color | 10 yellow 1.6 red | (Lovibond 5¼″) |

The preceding specific embodiments are illustrative of the practice of the invention. It is obvious, however, that other procedures known to those skilled in the art or disclosed herein may be employed without departing from the spirit of the invention or the scope of the appended claims.

We claim:

1. In a process for the non-degenerative distillation of $C_{6-24}$-fatty acids which are obtained by hydrolytically splitting natural fats and oils or by synthetic processes, removing water by thermally drying the crude product under reduced pressure, subjecting the dried and heated crude product to fractional evaporation in falling-film evaporators, in the presence of 0 to 10% by weight of the total feed of superheated steam, and condensing the resulting various vapor fractions in at least two condensers, the improvement comprising:

(a) conducting the thermal drying process at a temperature of 60° to 80° C. under a pressure of from 90 to 100 mbars;

(b) heating the dried crude product in a first falling-film evaporator to a temperature of 212° to 224° C. under a pressure of 5 to 20 mbars to evaporate the low-boiling fraction of said dried crude product, leaving a liquid residue;

(c) distilling said liquid residue, with recirculation distillation, to completion;

(d) passing the vapors from said distillation through a rectification column having baffles which show a pressure loss of at most 1 mbar per meter of packing height at a comparable air flow velocity of at least 2 m/s, said column comprising an upper separation stage having at least one separation sub-stage and a lower separation stage having at least three separation sub-stages, condensing the low-boiling constituents of said vapors in said upper stage as main runnings;

(e) condensing the remaining vapors in two sequential outlet condensers;

(f) returning the condensate from the first said outlet condenser to the head of the rectification column;

(g) drawing off said main runnings through an outlet as a sidestream from said rectification column;

(h) returning a partial return flow from a sidestream beneath said outlet for the main runnings; and (i) continuously removing a small quantity of residue from a second, circulation-type falling-film evaporator.

2. The process of claim 1 wherein up to 10% by weight of the total feed of superheated steam is introduced into the head of said second falling-film evaporator.

3. The process of claim 1 wherein said upper stage is above said main runnings sidestream and said lower stage is below said main runnings sidestream.

4. The process of claim 2 wherein said upper stage is above said main runnings sidestream and said lower stage is below said main runnings sidestream.

5. The process of claim 1 wherein from 0.5 to 5% of the total feed is removed as first runnings from the second of said at least two sequential outlet condensers.

6. The process of claim 2 wherein from 0.5 to 5% of the total feed is removed as first runnings from the second of said at least two sequential outlet condensers.

7. The process of claim 3 wherein from 0.5 to 5% of the total feed is removed as first runnings from the second of said at least two sequential outlet condensers.

8. The process of claim 4 wherein from 0.5 to 5% of the total feed is removed as first runnings from the second of said at least two sequential outlet condensers.

* * * * *